United States Patent [19]

Wuest et al.

[11] Patent Number: 4,801,733
[45] Date of Patent: Jan. 31, 1989

[54] 1-SUBSTITUTED TETRALIN DERIVATIVES, THEIR PREPARATION AND THEIR USE

[75] Inventors: Hans-Heiner Wuest, Dossenheim; Fritz-Frieder Frickel, Deidesheim; Axel Nuerrenbach, Gruenstadt, all of Fed. Rep. of Germany

[73] Assignee: BASF Aktiengesellschaft, Ludwigshafen, Fed. Rep. of Germany

[21] Appl. No.: 778,681

[22] Filed: Sep. 23, 1985

[30] Foreign Application Priority Data

Sep. 22, 1984 [DE] Fed. Rep. of Germany ....... 3434944

[51] Int. Cl.$^4$ .............................................. C07C 69/76
[52] U.S. Cl. ...................... 560/56; 562/466
[58] Field of Search .............. 560/56; 562/466; 514/544, 569

[56] References Cited

U.S. PATENT DOCUMENTS 4,326,055 4/1982 Loeliger ............................. 542/429
4,578,498 3/1986 Frickel et al. ....................... 560/65

FOREIGN PATENT DOCUMENTS 2854354 7/1979 Fed. Rep. of Germany .
3202118 7/1983 Fed. Rep. of Germany .

OTHER PUBLICATIONS

Loeliger et al. (1980) Arotinoids, A New Class of Highly Active Retinoids, Eur. J. Med. Chem. Chimica Therapeutica 15(1)–9–15.

Primary Examiner—Paul J. Killos
Attorney, Agent, or Firm—Keil & Weinkauf

[57] ABSTRACT 1-substituted tetralins of the formula I

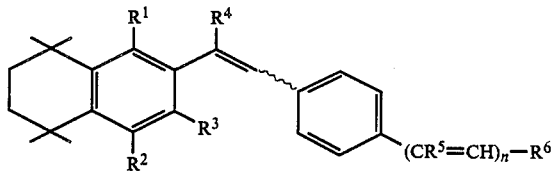

where n, $R^1$, $R^2$, $R^3$, $R^4$, $R^5$ and $R^6$ have the meanings stated in the description, and their preparation are described. The compounds are useful for the treatment of disorders.

11 Claims, No Drawings

1-SUBSTITUTED TETRALIN DERIVATIVES, THEIR PREPARATION AND THEIR USE

It has been disclosed (German Laid-Open Application Nos. DOS 2,854,353 and DOS 3,202,118) that stilbene derivatives have pharmacological effects in the topical and systemic therapy of neoplasias, acne, psoriasis and other dermatological affections. However, their action is not always satisfactory.

We have found that 1-substituted tetralins of the formula I

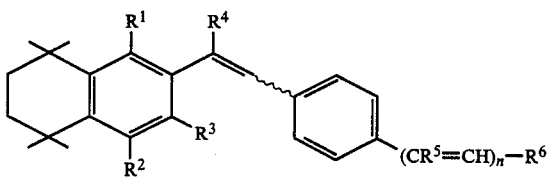

where n is 0 or 1, $R^1$ is hydroxyl, methyl or $C_1$–$C_6$-alkoxy, $R^2$ and $R^3$ are each hydrogen, halogen, $C_1$–$C_4$-alkyl or methoxy, $R^4$ is hydrogen or an acyclic or cyclic alkyl group of not more than 6 carbon atoms, $R^5$ is hydrogen or $C_1$–$C_4$-alkyl, and $R^6$ is hydrogen, nitrile, $C_2$–$C_{10}$-ketal, 2-oxazolinyl, tetrazolyl or a radical —$CHR^7R^8$ or —CO—$R^9$, where $R^7$ is hydrogen or $C_1$–$C_3$-alkyl $R^8$ is hydrogen or a radical —$OR^{10}$ or —$NR^{11}R^{12}$ (where $R^{10}$ is hydrogen, $C_1$–$C_4$-alkyl, $C_1$–$C_{20}$-alkanoyl, unsubstituted or substituted aralkyl or unsubstituted or substituted benzoyl, and $R^{11}$ and $R^{12}$ are each hydrogen, $C_1$–$C_4$-alkyl, $C_1$–$C_{20}$-alkanoyl or unsubstituted or substituted benzyl, or $R^{11}$ and $R^{12}$, together with the nitrogen atom to which they are bonded, form a heterocyclic radical), $R^9$ is hydrogen, halogen, $C_1$–$C_4$-alkyl, azido, imidazolyl, thiazolyl or a radical —$OR^{13}$ or —$NR^{14}R^{15}$ (where $R^{13}$ is hydrogen or $C_1$–$C_8$-alkyl which is unsubstituted or substituted by hydroxyl or $C_1$–$C_6$-alkoxy, or is an unsubstituted or substituted aryl or aralkyl group, and $R^{14}$ and $R^{15}$ are each hydrogen, $C_1$–$C_6$-alkyl, an unsubstituted or substituted aryl or aralkyl group or tetrazolyl, or $R^{14}$ and $R^{15}$, together with the nitrogen atom to which they are bonded, form a heterocyclic radical), and their physiologically tolerated salts have a better action spectrum.

Aryl is preferably phenyl, which may be substituted by methyl, methoxy or nitro. Aralkyl is preferably benzyl, which can be substituted in the aryl moiety by methyl, methoxy or halogen. Substituents of the benzoyl group can be, for example, methyl, methoxy or halogen. Preferred heterocyclic radicals are pyrrolidino, piperidino and morpholino. Halogen atoms $R^2$ and $R^3$ are preferably fluorine, and halogen atoms $R^{10}$ are preferably fluorine or chlorine.

Typical examples of compounds according to the invention are:

4-[2-(5,6,7,8-tetrahydro-1-methoxy-3,5,5,8,8-pentamethylnaphth-2-yl)-1-propylene]-benzoic acid 4-[2-(5,6,7,8-tetrahydro-1,3-dimethoxy-5,5,8,8-tetramethylnaphth-1-yl)-1-propylene]-benzoic acid 4-[2-(5,6,7,8-tetrahydro-1-methoxy-4,5,5,8,8-pentamethylnaphth-2-yl)-1-propenyl]-benzoic acid 4-[2-(5,6,7,8-tetrahydro-1,4-dimethoxy-5,5,8,8-tetramethylnaphth-2-yl)-1-propenyl]-benzoic acid 4-[2-(5,6,7,8-tetrahydro-1-hydroxy-3,5,5,8,8-pentamethylnaphth-2-yl)-1-propenyl]-benzoic acid 4-[2-(1-hexyloxy-5,6,7,8-tetrahydro-3,5,5,8,8-pentamethylnaphth-2-yl)-1-propenyl]-benzoic acid 4-[2-(1-ethoxy-5,6,7,8-tetrahydro-3,5,5,8,8-pentamethylnaphth-2-yl)-1-propenyl]-benzoic acid 4-[2-(5,6,7,8-tetrahydro-1,4-dimethoxy-3,5,5,8,8-pentamethylnaphth-2-yl)-1-propenyl]-benzoic acid 4-[2-(3fluoro-5,6,7,8-tetrahydro-1-methoxy-5,5,8,8-tetramethylnaphth-2-yl)-1-propenyl]-benzoic acid 4-[2-(3-chloro-5,6,7,8-tetrahydro-1-methoxy-5,5,8,8-tetramethylnaphth-2-yl)-1-propenyl]-benzoic acid 4-[2-(5,6,7,8-tetrahydro-1,3,5,5,8,8-hexamethylnaphth-2-yl)-1-propenyl]-benzoic acid 4-[2-(5,6,7,8-tetrahydro-1,3-dimethoxy-4,5,5,8,8-pentamethylnaphth-2-yl)-1-propenyl]-benzoic acid 4-[2-(5,6,7,8-tetrahydro-1-methoxy-3,5,5,8,8-pentamethylnaphth-2-yl)-1-ethenyl]-benzoic acid 4-[2-(5,6,7,8-tetrahydro-1,3-dimethoxy-5,5,8,8-tetramethylnaphth-2-yl)-1-ethenyl]-benzoic acid 4-[2-(5,6,7,8-tetrahydro-1,4-dimethoxy-5,5,8,8-tetramethylnaphth-2-yl)-1-ethenyl]-benzoic acid 4-[2-(5,6,7,8-tetrahydro-1-methoxy-4,5,5,8,8-pentamethylnaphth-2-yl)-1-ethenyl]-benzoic acid 4-[2-(5,6,7,8-tetrahydro-1-hydroxy-3,5,5,8,8-pentamethylnaphth-2-yl)-1-ethenyl]-benzoic acid 4-[2-(1-hexyloxy-5,6,7,8-tetrahydro-3,5,5,8,8-pentamethylnaphth-2-yl)-1-ethenyl]-benzoic acid 4-[2-(1-ethoxy-5,6,7,8-tetrahydro-3,5,5,8,8-pentamethylnaphth-2-yl)-1-ethenyl]-benzoic acid 4-[2-(5,6,7,8-tetrahydro-1,4-dimethoxy-3,5,5,8,8-pentamethylnaphth-2-yl)-1-ethenyl]-benzoic acid 4-[2-(3-fluoro-5,6,7,8-tetrahydrol-1-methoxy-5,5,8,8-tetramethylnaphth-2-yl)-1-ethenyl]-benzoic acid 4-[2-(5,6,7,8-tetrahydro-1,4,5,5,8,8-hexamethylnaphth-2-thyl)-1-propenyl]-benzoic acid 4-[2-(5,6,7,8-tetrahydro-1-methoxy-3,5,5,8,8-pentamethylnaphth-2-yl)-1-buten-1-yl]-benzoic acid 4-[2-(5,6,7,8-tetrahydro-1,3-dimethoxy-5,5,8,8-tetramethylnaphth-2-yl)-1-buten-1-yl]-benzoic acid 4-[2-(5,6,7,8-tetrahydro-1,4-dimethoxy-5,5,8,8-tetramethylnaphth-2-yl,-1-buten-1-yl]-benzoic acid 4-[3-methyl-2-(5,6,7,8-tetrahydro-1-methoxy-3,5,5,8,8-pentamethylnaphth-2-yl)-1-buten-1-yl]-benzoic acid 4-[2-cyclopropyl-2-(5,6,7,8-tetrahydro-1-methoxy-3,5,5,8,8-pentamethylnaphth-2-yl)-1-ethenyl]-benzoic acid 4-[2-(5,6,7,8-tetrahydro-1-methoxy-3,5,5,8,8-pentamethylnaphth-2-yl)-1-hexen-1-yl]-benzoic acid 4-[2-cyclohexyl-2-(5,6,7,8-tetrahydro-1-methoxy-3,5,5,8,8-pentamethylnaphth-2-yl)-1-ethenyl]-benzoic acid In these compounds, other typical radicals apart from the carboxyl group are: methoxycarbonyl, ethoxycarbonyl, propyloxycarbonyl, butoxycarbonyl, benzyloxycarbonyl, azidocarbonyl, chlorocarbonyl, fluorocarbonyl, cyano, formyl, hydroxymethyl, methyl, acetyl, methoxymethyl, ethoxymethyl, benzyloxymethyl, formyloxymethyl, acetoxymethyl, propionyloxymethyl, hexadecanoyloxymethyl, benzyloxymethyl, 3,4-dimethoxybenzyloxymethyl, aminoethyl, methylaminomethyl, ethylaminomethyl, propylaminomethyl, butylaminomethyl, acetylaminomethyl, formylaminomethyl, benzoylaminomethyl, 4-methoxybenzoylaminomethyl, dimethylaminomethyl, morpholinomethyl, pyrrolidinomethyl, piperidinomethyl, oxazolin-2-yl, 1,3-dioxolan-2-yl, dimethoxymethyl, (E)-2-carbethoxyethenyl, (E)-2-carboxyethenyl, hydrogen, carbamyl, methylcarbamyl, dimethylcarbamyl, morpholinocarbamyl, benzylcarbamyl, phenylcarbamyl and tetrazolyl.

The compounds according to the invention can be prepared in various ways, each of which is known in principle. For example, a carbonyl compound of the formula II

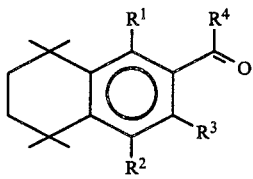

where $R^1$, $R^2$, $R^3$ and $R^4$ have the stated meanings, can be subjected to a Wittig-Horner reaction with a phosphorus compound of the formula III

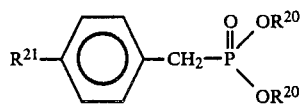

where $R^{21}$ is hydrogen, $C_1$-$C_4$-alkyl, nitrile or —$COOR^{22}$, and $R^{20}$ and $R^{22}$ are each $C_1$-$C_3$-alkyl. Advantageously, the reaction is carried out in a solvent in the presence of a basic compound conventionally employed for Wittig-Horner reactions.

The Wittig-Horner reaction is carried out at no higher than 100° C., advantageously from 20° to 50° C., under atmospheric pressure or in a closed vessel under superatmospheric pressure, if necessary with heating to the stated temperature.

This reaction can be effected in the presence of a diluent or solvent, for example a lower saturated dialkyl ether, dialkylglycol ether or cyclic ether, such as diethyl ether, ethyl tert.-butyl ether, 1,2-dimethoxyethane, tetrahydrofuran or dioxane, an aromatic hydrocarbon, such as benzene or an alkylbenzene, eg. toluene or xylene, a saturated aliphatic hydrocarbon, such as hexane, heptane or isooctane, a lower aliphatic ketone, such as acetone, methyl ethyl ketone or methyl isobutyl ketone, a dialkylformamide, such as dimethylformamide or diethylformamide, or a mixture of the stated solvents. Cyclic ethers, such as dioxane or tetrahydrofuran, and in particular dimethylformamide, or a mixture of these, are preferably used, the reaction taking place in general at no higher than 30° C.

Reactions are carried out in the presence of a deprotonating agent for the phosphate (III), suitable compounds being alkali metal hydrides and alkali metal amides, in particular those of sodium and of potassium, the sodium and potassium salts of dimethyl sulfoxide, alkyl-lithium compounds, such as n-butyl-lithium, and alkali metal alcoholates, preferably sodium methylate or ethylate.

The compounds according to the invention may furthermore be obtained by subjecting a phosphonium salt of the formula IV

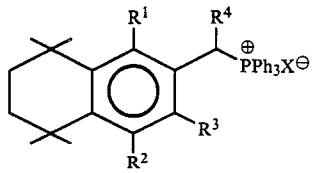

where $R^1$, $R^2$, $R^3$ and $R^4$ have the above meanings and $X^\ominus$ is an anion, preferably chloride or bromide, to a Wittig reaction with a p-carbalkoxybenzaldehyde of the formula V

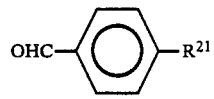

where $R^{21}$ has the stated meanings.

The Wittig or Wittig-Horner reaction usually gives a mixture of the steric (E/Z) isomers of the olefins.

On exposure to light, E/Z isomer mixtures containing a predominant amount of the Z isomer undergo rearrangement at the olefinic double bond to give mixtures having a higher content of the E isomer. The resulting (E/Z) isomer mixtures which then have a more favorable content of the E isomer are advantageously converted to pure E compounds of the formula (I), preferably by crystallization or a chromatographic method, such as column chromatography or preparative HPLC.

The photoisomerization is preferably carried out in solution, suitable solvents being polar protic and aprotic solvents, eg. methanol, ethanol, ethyl acetate, tetrahydrofuran or acetone. The concentration of the irradiated solution is from 0.1 to 50, preferably from 1 to 15, percent by weight.

Irradiation can be effected in the presence of a sensitizer, eg. acetophenone, 4-methoxyacetophenone, propiophenone, benzene, acetone, benzophenone, benzil or Michler's ketone. Acetone is particularly preferred for this purpose.

Preferred light sources for carrying out the stated photoreaction are artificial radiation sources which emit some or all of their radiation in the range from 200 to 600 nm, preferably from 300 to 400 nm. Mercury vapor lamps, fluorine lamps, xenon lamps, tungsten lamps, fluorescent tubes and carbon arc lamps are advantageous.

The irradiation temperature is dependent on the type of solvent used, but is particularly preferably from +10° to +30° C. The radiant heat can be removed by cooling the lamp and/or cooling the reaction mixture. Distilled water or filtered solutions provided with conventional additives can be employed in the cooling circulation of the lamp.

The ketones and aldehydes of the formula II which are required for the Wittig-Horner reaction can be prepared by acylating the corresponding tetrahydrotetramethylnaphthalenes in the presence of a Lewis acid, particularly suitable acylating agents being acyl halides, mainly acyl chlorides. Preferred Lewis acids are iron-(III) chloride, aluminum(III) chloride and titanium(IV) chloride. The formylation can advantageously be carried out using hexamethylenetetramine/trifluoroacetic acid. The tetrahydrotetramethylnaphthalenes are described in U.S. Pat. Nos. 3,442,640 and 3,499,751, or can be prepared from 2,5-dichloro-2,5-dimethylhexane and an appropriately substituted benzene by Friedel-Crafts alkylation using the method described therein.

The phosphonium salts of the formula IV can be obtained as follows: a carbonyl compound of the formula II is first reduced with a complex metal hydride, such as sodium borohydride or lithium aluminum hydride, to give the corresponding alcohol, which is then halogenated with a phosphorus halide, such as phosphorus tribromide or phosphorus oxychloride, in the presence of a base, such as pyridine. Subsequent reaction with triphenylphosphine gives the phosphonium salt of the formula IV.

The benzoates of the general formula I, in which $n=0$ and $R^6$ is carboalkoxy, are, if desired, converted to the free carboxylic acids and their physiologically tolerated salts by hydrolysis of the esters. Conversely, the free acid can of course be esterified in a conventional manner.

Advantageously, the hydrolysis/esterification is carried out in the presence of a diluent or solvent, for example a dialkylglycol ether or cyclic ether, such as 1,2-dimethoxyethane, tetrahydrofuran or dioxane, a lower aliphatic ketone, such as acetone, methyl ethyl ketone or methyl isobutyl ketone, or a lower aliphatic alcohol, such as methanol, ethanol, propanol or isopropanol, in the presence or absence of water, or in a mixture of the stated solvents with water.

Preferred solvents are aqueous mixtures of ethanol and methanol, the reaction being carried out at the boiling point of the reaction mixture.

Hydrolysis is preferably effected in the presence of an alkali, such as an alkali metal hydroxide, an alkali metal carbonate or an alkali metal bicarbonate, in particular of sodium or of potassium, a tertiary organic base, such as pyridine or a lower trialkylamine, eg. trimethylamine or triethylamine, as a mixture with water. The base is used in a stoichiometric amount or in slight excess, based on the ester. Sodium hydroxide or potassium hydroxide is preferably used.

The amides according to the invention can be prepared in a conventional manner by first converting the corresponding benzoic acids to derivatives possessing a more active carbonyl group, for example to the acyl halides, azides, amidazolides or anhydrides, the O-acyl-N,N'-dicyclohexylisoureas or p-nitrophenyl esters, and then treating these with an amine $HNR^{11}R^{12}$. In the case of particularly reactive amines, especially ammonia, direct amidolysis of esters (containing a radical $-OR^{10}$) is preferred.

A halide of a carboxylic acid, preferably an acyl chloride, can be converted to an oxazoline derivative of the formula I by reaction with 2-aminoethanol followed by cyclization.

A carboxylic acid, a carboxylate or a carboxamide of the formula I can be reduced to the corresponding alcohol or amine in a conventional manner. Advantageously, the reduction is effected with the aid of a metal hydride or alkali metal hydride in the presence of a suitable solvent. Preferably used metal hydrides are complex metal hydrides, such as lithium, aluminum hydride or diisobutyl-aluminum hydride. Where lithium aluminum hydride is employed, ethers, such as diethyl ether, dioxane or tetrahydrofuran, are used as solvents. If the reduction is carried out using diisobutyl-aluminum hydride or an alkoxysodium aluminum hydride, hydrocarbons, such as hexane or toluene are preferably used.

An amine or an alcohol of the formula I can be converted to the novel amides or esters in a conventional manner using an alkanoyl halide or anhydride, an aralkyl halide or anhydride or an aroyl or hetaroyl halide or anhydride, advantageously in an inert diluent or solvent, for example a lower aliphatic ketone, such as acetone, methyl ethyl ketone or methyl isobutyl ketone, a dialkylformamide, such as dimethylformamide or diethylformamide, or using escess acylating agent as the diluent or solvent. The reactions are preferably carried out in the presence of a base as acid acceptor, at from $-20°$ C. to the boiling point of the reaction mixture. Suitable bases are alkali metal carbonates, bicarbonates, hydroxides and alcoholates, in particular those of sodium and of potassium, basic oxides, such as aluminum oxide or calcium oxide, tertiary organic bases, such as pyridine, and lower trialkylamines, eg. trimethylamine and triethylamine. The base can be used in a catalytic amount or in a stoichiometric amount or a slight excess, based on the alkylating agent employed.

An alcohol of the formula I can be reacted with an alkyl halide $R^{12}I$, $R^{12}Br$ or $R^{12}Cl$ in the presence of an alkali metal hydride, preferably sodium hydride, or in the presence of an alkyl-lithium compound, preferably n-butyl-lithium, in an organic solvent, such as tetrahydrofuran, dioxane, 1,2-dimethoxyethane, methyl tert.-butyl ether or, where sodium hydride is used, dimethylformamide, at from $-10°$ to $40°$ C. to give an ether of the formula I.

An alcohol of the formula I can be oxidized to an aldehyde of the formula I with a suitable oxidizing agent, preferably manganese(IV) oxide, if appropriate on an inorganic carrier, such as silica gel or alumina. Advantageously, the reaction is carried out in an inert organic solvent, for example a hydrocarbon, such as hexane, or an ether, eg. tetrahydrofuran, or a mixture of the stated solvents and diluents, at from $-10°$ to $30°$ C. The reaction time required depends substantially on the oxidation activity of the manganese(IV) oxide employed.

An aldehyde of the formula I can be obtained by reducing the corresponding nitrile of the formula I with disobutyl-aluminum hydride in a solvent, preferably toluene, hexane, tetrahydrofuran or a mixture of these, at from $-40°$ C. to room temperature.

A carbonyl compound of the formula I (where $n=0$) can be subjected to a Wittig-Horner reaction with a phosphorus compound of the formula VI or VII

VI

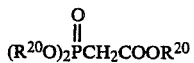

VII where $R^{20}$ has the stated meanings, the reaction advantageously being carried out in a solvent, preferably tetrahydrofuran, dimethylformamide or dimethyl sulfoxide, and in the presence of a base conventionally used for such olefinations, eg. sodium hydride or sodium methylate. The reaction takes place at no higher than $100°$ C., advantageously at from $20°$ to $50°$ C.

The nitrile or ester group is, if desired, then converted to other functional groups by the methods described above or below.

A nitrile of the formula I can be hydrolysed to the corresponding carboxylic acid in a conventional manner with acid catalysis, or advantageously, base catalysis. Preferred bases are alkali metal hydroxides, particularly potassium hydroxide, which is used in excess. As a rule, water-miscible alcohols, eg. methanol, ethanol, isopropanol or n-butanol, are used as solvents. The reaction is usually carried out at the boiling point of the reaction mixture.

The nitriles of the formula I can be converted to the corresponding tetrazoles of the formula I by means of an addition reaction with an azide, for example an alkali metal azide, preferably sodium azide, in the presence of aluminum chloride or ammonium chloride. Preferably used solvents are cyclic ethers, such as dioxane or tetrahydrofuran, and in particular dimethylformamide or a mixture of these, the reaction being carried out in general at from 60° to 100° C.

Some of the novel compounds possess an acidic hydrogen atom and can therefore be converted with a base, in a conventional manner, to a physiologically tolerated, readily water-soluble salt. Examples of suitable salts are ammonium salts, alkali metal salts, in particular those of sodium, of potassium and of lithium, alkaline earth metal salts, in particular those of calcium and magnesium, and salts with suitable organic bases, such as lower alkylamines, eg. methylamine, ethylamine or cyclohexylamine, with substituted lower alkylamines, in particular hydroxyl-substituted alkylamines, such as diethanolamine, triethanolamine or tris(hydroxymethyl)aminomethane, and with piperidine and morpholine.

If desired, the resulting novel amines of the formula (I) are converted to an addition salt with a physiologically tolerated acid by a conventional procedure. Examples of suitable conventional physiologically tolerated inorganic acids are hydrochloric acid, hydrobromic acid, phosphoric acid and sulfuric acid, and examples of organic acids are oxalic acid, maleic acid, fumaric acid, lactic acid, tartaric acid, malic acid, citric acid, salicylic acid, adipic acid and benzoic acid. Other suitable acids are described in Forthschritte der Arzneimittelforschung Volume 10, pages 224–225, Birkhauser Verlag, Basel and Stuttgart, 1966.

Because of their pharmacological properties, the novel compounds and their physiologically tolerated salts can be used in the topical and systemic therapy and prophylaxis of precanceroses and carcinomas of the skin, the mucous membranes and internal organs, in the topical and systemic therapy of acne, psoriasis and other dermatological disorders accompanied by pathologically changed cornification, and for the treatment of rheumatic disorders, in particular those of an inflammatory or degenerative nature which affect the joints, muscles, tendons and other parts of the locomotor system. A preferred area of indication in addition to the therapy of dermatological disorders is the prophylactic and therapeutic treatment of precanceroses and tumors.

The pharmacological effects can be demonstrated, for example, in the following test models. In in vitro hamster tracheal tissue, the novel compounds eliminate the keratinization which sets in after vitamin A deficiency. This keratinization forms part of the early phase of carcinogenesis, which is inhibited in vivo by the novel compounds of the formula (I) using a similar technique after being induced by chemical compounds or high-energy radiation or after viral cell transformation. This method is described in Cancer Res. 36 (1976), 964–972, Nature 250 (1974), 64–66 and Nature 253 (1975), 47–50.

The compounds according to the invention also inhibit the proliferation rates of certain cells showing malignant changes. This method is described in J. Natl. Cancer Inst. 60 (1978), 1035–1041, Experimental Cell Research 117 (1978), 15–22 and Proc. Natl. Acad. Sci. USA 77 (1980), 2937–2940.

The antiarthritic action of the novel compounds can be determined in a conventional manner in animal experiments using the adjuvant arthritis model. The dermatological activity, for example in the treatment of acne, can be demonstrated by, inter alia, determining the comedolytic activity and the ability to reduce the number of cysts in the rhino mouse model.

This method is described by L. H. Kligman et al. in The Journal of Investigative Dermatology 73 (1978), 354–358, and J. A. Mezick et al. in Models of Dermatology (Ed. Maibach, Lowe), vol. 2, pages 59–63, Karger, Basel 1985].

The test substance in a suitable carrier was applied topically (100 μl) to the entire back area of the Rhino mouse, application being effected once a day on five successive days per week for two weeks. About 72 hours after the final treatment, the dorsal skin was removed, and left in 0.5% strength acetic acid for 18 hours at 4°–6° C. Thereafter, an area of about 2×5 cm² was cut out and the epidermis was peeled off, placed on a microscope slide (with the dermal side upward) and washed water-free with alcohol/xylene until the epidermis appeared transparent. The sample was fixed by coating it with Permount, and evaluated microscopically. The diameters of 10 utricles in 5 freely selected areas were measured in each case, and the mean reduction in the utricle diameter was calculated from this by comparison with the untreated control group. The Table below shows the results obtained.

TABLE

| Substance | Dose mg/ml | Reduction in the utricle diameter in % |
|---|---|---|
| Example 17 | 2 | 68.6 |
|  | 0.2 | 53.9 |
| Example 19 | 2 | 72.5 |
|  | 0.2 | 56.0 |
| Example 16 | 1 | 73.6 |
|  | 0.1 | 49.8 |
| Example 14 | 1 | 77.5 |
|  | 0.1 | 55.0 |

Accordingly, the present invention furthermore relates to therapeutic agents for topical and systemic administration which contain a compound of the formula (I) as an active compound, in addition to conventional carriers or diluents, and to the use of a compound of the formula (I) for the preparation of a drug.

The therapeutic agents or formulations are prepared in a conventional manner, for example by mixing an appropriate dose of the active compound with conventional solid or liquid carriers or diluents and conventional pharmaceutical auxiliaries, in accordance with the desired route of administration.

Accordingly, the agents can be administered perorally, parenterally or topically. Examples of formulations of this type are tablets, film tablets, coated tablets, capsules, pills, powders, solutions or suspensions, infusion or injectable solutions, and pastes, ointments, gels, creams, lotions, dusting powders, solutions or emulsions and sprays.

The therapeutic agents can contain the compounds used according to the invention in a concentration of from 0.001 to 1%, preferably from 0.001 to 0.1%, for local administration, and preferably in a single dose of from 0.1 to 50 mg for systemic administration, and can be administered daily in one or more doses, depending on the nature and severity of the illness.

Examples of conventional pharmaceutical auxiliaries are alcohols, such as isopropanol, oxyethylated castor oil or oxethylated hydrogenated castor oil, polyacrylic acid, glycerol monostearate, liquid paraffin, vaseline, wool fat, polyethylene glycol 400, polyethylene glycol 400 stearate and oxyethylated fatty alcohols for local administration, and lactose, propylene glycol, ethanol, starch, talc and polyvinylpyrrolidone for systemic administration. If required, an antioxidant, for example tocopherol, butylated hydroxyanisole or butylated hydroxytoluene, or flavor-improving additives, stabilizers, emulsifiers, lubricants, etc. may be added to the preparations. All substances must be toxicologically acceptable and compatible with the active compounds used.

PREPARATION OF THE COMPOUNDS ACCORDING TO THE INVENTION

A.

Preparation of starting compounds

2-Formyl-5,6,7,8-tetrahydro-1-alkoxy-3,5,5,8,8-pentamethylnaphthalene 340 ml of dimethyl sulfoxide and 32.2 g of potassium hydroxide (pellets) are stirred for 5 minutes, after which 0.1 mole of 2-formyl-5,6,7,8-tetrahydro-3,5,5,8,8-pentamethylnaphth-1-ol and 0.24 mole of an alkylhalide are added in succession, the temperature increasing slightly. The mixture is stirred overnight at room temperature and then extracted with ether/water. The ether phase is washed several times with water, dried over $Na_2SO_4$ and evaporated down. The resulting crude product is, if necessary, purified by distillation.

The following compounds are prepared by this process.

1-ethoxy-2-formyl-5,6,7,8-tetrahydro-3,5,5,8,8-pentamethylnaphthalene, bp. 130°–132° C. (0.2 mbar), yield 87%.

2-formyl-5,6,7,8-tetrahydro-3,5,5,8,8-pentamethyl-1-propoxynaphthalene, yield 100% (crude)

1-(2-methylethoxy)-2-formyl-5,6,7,8-tetrahydro-3,5,5,8,8-pentamethylnaphthalene, bp. 112°–117° C. (0.1 mbar), yield 70%

1-butoxy-2-formyl-5,6,7,8-tetrahydro-3,5,5,8,8-pentamethylnaphthalene, bp. 140° C. (0.2 mbar), yield 82%

2-formyl-1-hexyloxy-5,6,7,8-tetrahydro-3,5,5,8,8-pentamethylnaphthalene, yield 100% (crude).

B.

Preparation of the end products

EXAMPLE 1

Ethyl (E)-4-[2-(5,6,7,8-tetrahydro-1-methoxy-3,5,5,8,8-pentamethylnaphth-2-yl)-1-ethenyl]-benzoate A solution of 7.5 g (25 millimoles) of diethyl 4-carboxyethylbenzylphosohate in 12 ml of dimethyl sulfoxide was added dropwise to a suspension of 25 ml of absolute dimethyl sulfoxide and 0.75 g (25 millimoles) of sodium hydride (80% strength, freed beforehand from the 20% of paraffin using petroleum ether), the dropwise addition being begun at room temperature. The mixture was then stirred for a further 30 minutes at from 35° to 40° C., after which 3 g (12.5 millimoles) of 2-formyl-5,6,7,8-tetrahydro-1-methoxy-3,5,5,8,8-pentamethylnaphthalene, dissolved in 12 ml of dimethyl sulfoxide and 1 ml of tetrahydrofuran, were added dropwise in the course of 10 minutes and stirring was continued for 3 hours at room temperature. The mixture was then poured onto 300 ml of water and acidified with 2N hydrochloric acid, the greasy residue was separated off and stirred with methanol, and the product was filtered off. Purification of the solid by column chromatography (silica gel, toluene) gave 1.9 g of the title compound of melting point 123.2° C.

HPLC analysis (Si 60, 5 $\mu$m, 150 bar, 97:3 n-heptane/ethyl acetate, $t_R=6.7$ min) showed that the product consisted of more then 98% of a single isomer.

EXAMPLE 2

(E)-4-[2-(5,6,7,8-Tetrahydro-1-methoxy-3,5,5,8,8-pentamethylnaphth-2-yl)-1-ethenyl]-benzonitrile A solution of 25.2 g (0.1 mole) of diethyl 4-cyanobenzylphosphonate in 50 ml of dimethyl sulfoxide was added dropwise to a suspension of 3 g (0.1 mole) of sodium hydride (80% strength, freed beforehand from the 20% of paraffin using petroleum ether) in 100 ml of absolute dimethyl sulfoxide at from 25° to 40° C. The mixture was stirred for a further hour, after which a solution of 12 g (50 millimoles) of 2-formyl-5,6,7,8-tetrahydro-1-methoxy-3,5,5,8,8-pentamethylnaphthalene in 100 ml of dimethyl sulfoxide was added dropwise, and the mixture was stirred overnight at room temperature. Thereafter, the reaction mixture was poured onto 1.2 l of water and acidified with 2N hydrochloric acid, the resulting oily product was separated off and stirred with a little methanol, the crystals obtained were filtered off and the solid was washed on the filter with methanol and dried to give 13.8 g of the title compound of melting point 120° C.

EXAMPLE 3

(E)-4-[2-(5,6,7,8-tetrahydro-1-methoxy-3,5,5,8,8-pentamethylnaphth-2-yl)-1-ethenyl]-benzoic acid 5.1 g (15 millimoles) of (E)-4-[2-(5,6,7,8-tetrahydro-1-methoxy-3,5,5,8,8-pentamethylnaphth-2-yl)-1-ethenyl]-benzonitrile from Example 2, 75 ml of ethanol and 75 ml of 10N sodium hydroxide solution were refluxed until the reaction was complete, this taking about 3 hours. The reaction mixture was cooled and then poured onto 750 ml of ice/water and neutralized with concentrated hydrochloric acid. The resulting solid was filtered off under suction, washed neutral with water, washed with methanol and dried in a stream of nitrogen to give 3.5 g of the title compound of melting point 222°–223° C. (ethanol/$H_2O$).

The compounds shown in the Table below were prepared either by a Wittig-Horner reaction (similarly to Example 2) or by hydrolysis of the corresponding nitriles (similarly to Example 3):

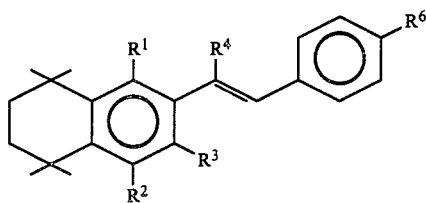

| No. | Name | R¹ | R² | R³ | R⁴ | R⁶ | Yield (%) | Mp. (°C.) |
|---|---|---|---|---|---|---|---|---|
| 4 | (E)—4-[2-(5,6,7,8-tetrahydro-1-methoxy-4,5,5,8,8-pentamethyl-2-naphthyl)-1-ethenyl]-benzonitrile | OCH₃ | CH₃ | H | H | CN | 72 | 120 |
| 5 | (E)—4-[2-(5,6,7,8-tetrahydro-1,3-dimethoxy-5,5,8,8-tetramethyl-2-naphthyl)-1-ethenyl]-benzonitrile | OCH₃ | H | OCH₃ | H | CN | 99 | 168–173 |
| 6 | (E)—4-[2-(5,6,7,8-tetrahydro-1,4-dimethoxy-5,5,8,8-tetramethyl-2-naphthyl)-1-ethenyl]-benzonitrile | OCH₃ | OCH₃ | H | H | CN | 70 | 154–158 |
| 7 | (E)-4-[2-(1-ethoxy-5,6,7,8-tetrahydro-3,5,5,8,8-pentamethyl-2-naphthyl)-1-ethenyl]-benzonitrile | OC₂H₅ | H | CH₃ | H | CN | 80 | 124–126 |
| 8 | (E)—4-[2-(5,6,7,8-tetrahydro-3,5,5,8,8-pentamethyl-1-propyloxy-2-naphthyl)-1-ethenyl]-benzonitrile | O—nC₃H₇ | H | CH₃ | H | CN | 79 | 98–100 |
| 9 | (E)-4-[2-(1-(2-methyl)ethoxy-5,6,7,8-tetrahydro-3,5,5,8,8-pentamethyl-2-naphthyl)-1-ethenyl]-benzonitrile | O—iC₃H₇ | H | CH₃ | H | CN | 61 | 116–118 |
| 10 | (E)—4-[2-(1-butyloxy-5,6,7,8-tetrahydro-3,5,5,8,8-pentamethyl-2-naphthyl)-1-ethenyl]-benzonitrile | O—nC₄H₉ | H | CH₃ | H | CN | 88 | 113–114 |
| 11 | (E)—4-[2-(1-hexyloxy-5,6,7,8-tetrahydro-3,5,5,8,8-pentamethyl-2-naphthyl)-1-ethenyl]-benzonitrile | O—nC₆H₁₃ | H | CH₃ | H | CN | 46 | 90–93 |
| 12 | (E)—1-[2-(5,6,7,8-tetrahydro-1,3-dimethoxy-5,5,8,8-tetramethyl-2-naphthyl)-2-(4-methyl)phenylethene | OCH₃ | H | OCH₃ | H | CH₃ | 79 | 84–86 |
| 13 | (E)—4-[2-(5,6,7,8-tetrahydro-1-methoxy-4,5,5,8,8-pentamethyl-2-naphthyl)-1-ethenyl]-benzoic acid | OCH₃ | CH₃ | H | H | COOH | 92 | 208 (decomposition) |
| 14 | (E)—4-[2-(5,6,7,8-tetrahydro-1,3-dimethoxy-5,5,8,8-tetramethyl-2-naphthyl)-1-ethenyl]-benzoic acid | OCH₃ | H | OCH₃ | H | COOH | 51 | 212 |
| 15 | (E)—4-[2-(5,6,7,8-tetrahydro-1,4-dimethoxy-5,5,8,8-tetramethyl-2-naphthyl)-1-ethenyl]-benzoic acid | OCH₃ | OCH₃ | H | H | COOH | 100 | 80–81 |
| 16 | (E)—4-[2-(1-ethoxy-5,6,7,8-tetrahydro-3,5,5,8,8-pentamethyl-2-naphthyl)-1-ethenyl]-benzoic acid | OC₂H₅ | H | OCH₃ | H | COOH | 94 | 144–145 |
| 17 | (E)—4-[2-(5,6,7,8-tetrahydro-3,5,5,8,8-pentamethyl-1-propyloxy-2-naphthyl)-1-ethenyl]-benzoic acid | O—nC₃H₇ | H | OCH₃ | H | COOH | 97 | 161–162 |
| 18 | (E)—4-[2-(1-(2-methyl)ethoxy-5,6,7,8-tetrahydro-3,5,5,8,8-pentamethyl-2-naphthyl)-1-ethenyl]-benzoic acid | O—iC₃H₇ | H | OCH₃ | H | COOH | 100 | 203 |
| 19 | (E)—4-[2-(1-butyloxy-5,6,7,8-tetrahydro-3,5,5,8,8-pentamethyl-2-naphthyl)-1-ethenyl]-benzoic acid | O—nC₄H₉ | H | OCH₃ | H | COOH | 99 | 210–211 |
| 20 | (E)—4-[2-(1-hexyloxy-5,6,7,8-tetrahydro-3,5,5,8,8-pentamethyl-2-naphthyl)-1-ethenyl]-benzoic acid | O—nC₆H₁₃ | H | OCH₃ | H | COOH | 97 | 133–138 |

EXAMPLE 21

(E)-4-[2-(5,6,7,8-Tetrahydro-1,3-dimethoxy-5,5,8,8-tetramethylnaphth-2-yl)-1-ethenyl]-benzoic acid azide 3.4 ml of triethylamine in 17 ml of acetone, followed by 2.6 ml (27 millimoles) of ethyl chloroformate, were added dropwise to a solution of 7.7 g (20 millimoles) of the carboxylic acid from Example 14 in 35 ml of acetone at 0° C. The mixture was stirred for a further 40 minutes at this temperature, after which a solution of 2 g (31.4 millimoles) of sodium azide in 4.3 ml of water was added dropwise, likewise at 0° C. Stirring was continued for a further 2 hours at this temperature, after which the crystals were filtered off under suction, washed with water and ethanol and dried to give 6.6 g of the title compound of melting point 125°–126° C. (decomposition).

EXAMPLE 22

(E)-4-[2-(5,6,7,8-Tetrahydro-1,3-dimethoxy-5,5,8,8-tetramethylnaphth-2-yl)-1-ethenyl]-benz(2-hydroxyethyl)amide 16 ml of ethanolamine were added dropwise to a solution of 3 g (8 millimoles) of the acid azide described in Example 21, in 200 ml of absolute tetrahydrofuran. The mixture was left to stand for 1.5 hours, after which it was partially evaporated down and the residue was poured onto water. The mixture was acidified with 2N HCl, and the precipitated solid was filtered off under suction, washed several times with water and a little methanol and dried. 2.7 g of the title compound of melting point 201°–203° C. were obtained in this manner.

EXAMPLE 23

(E)-4-[2-(5,6,7,8-Tetrahydro-1,3-dimethoxy-5,5,8,8-tetramethylnaphth-2-yl)-1-ethenyl]-benz(n-butyl)amide Using a method similar to that described in Example 22, 3 g (7.7 millimoles) of the acid azide described in Example 21 and 30 ml of n-butylamine were converted to the title compound, 2.3 g of product of melting point 137°–140° C. being obtained after recrystallization from methanol.

EXAMPLE 24

(E)-4-[2-(5,6,7,8-Tetrahydro-1,3-dimethoxy-5,5,8,8-tetramethylnaphth-2-yl)-1-ethenyl]-benzamide A mixture of 2 g (5.3 millimoles) of the nitrile from Example 5, 5 g of potassium hydroxide powder and 40 ml of tert.-butanol was refluxed for 20 minutes. The reaction mixture was cooled, poured onto saturated sodium chloride solution and then extracted twice with ether. The ether phases were dried over Na$_2$SO$_4$ and evaporated down, and the resulting residue was recrystallized from methanol to give 0.9 g of the title compound of melting point 190°–194° C.

EXAMPLE 25

Methyl (E)-4-[2-(5,6,7,8-tetrahydro-1,3-dimethoxy-5,5,8,8-tetramethylnaphth-2-yl)-1-ethenyl]-benzoate 7.2 ml (60 millimoles) of thionyl chloride in 10 ml of tetrahydrofuran were added dropwise to a solution of 11.8 g (30 millimoles) of the carboxylic acid from Example 14 in 120 ml of absolute tetrahydrofuran and 2.7 ml (56 millimoles) of pyridine. After a reaction time of 3 hours, the solution was filtered off from the pyridine hydrochloride, and the filtrate was added dropwise to 10 ml of absolute methanol. Stirring was continued overnight at room temperature, after which the mixture was poured onto water and extracted three times with ether. The ether phases were washed twice with water, dried over Na$_2$SO$_4$ and evaporated down, and the residue was recrystallized from methanol to give 5.5 g of the title compound of melting point 140°–142° C.

EXAMPLE 26

(E)-4-[2-(5,6,7,8-Tetrahydro-1,3-dimethoxy-5,5,8,8-tetramethylnaphth-2-yl)-1-ethenyl]-benzaldehyde 47.3 ml (57 millimoles) of DIBAH solution (20% strength in hexane) were added to a solution of 10.2 g (27 millimoles) of the nitrile from Example 5 in 100 ml of absolute ether at room temperature. The mixtue was stirred for a further 40 minutes, after which 150 ml of saturated tartaric acid solution were added dropwise. After 1 hour, the mixture was extracted three times with ether, and the ether phases were washed twice with water, dried over Na$_2$SO$_4$ and evaporated down. The residue was recrystallized twice from isopropanol, and 4.5 g of the title compound of melting point 108° C. were obtained.

EXAMPLE 27

(E)-4-[2-(5,6,7,8-Tetrahydro-1,3-dimethoxy-5,5,8,8-tetramethylnaphth-2-yl)-1-ethenyl]-benzyl alcohol A suspension of 14 g (35.5 millimoles) of the carboxylic acid from Example 14 in 116 ml of ether was added dropwise to a suspension of 1.6 g (42 millimoles) of lithium aluminum hydride in 200 ml of absolute ether, the mixture boiling gently. The mixture was stirred under reflux for 3 hours and then cooled, after which 50 ml of ethyl acetate, 100 ml of water and 150 ml of 2N HCl were added in succession. The phases were separated, and the aqueous phase was extracted twice with ether. The combined ether phases were washed neutral, dried over Na$_2$SO$_4$ and evaporated down. The crude mixture was first recrystallized from heptane and then subjected to flash chromatography (Si60, heptane with increasing amounts of ethyl acetate). 6.5 g of the title compound of melting point 102°–104° C. were obtained in this manner.

EXAMPLE 28

(E)-4-[2-(5,6,7,8-Tetrahydro-1,3-dimethoxy-5,5,8,8-tetramethylnaphth-2-yl)-1-ethenyl]-benzyl methyl ether 3.8 g (10 millimoles) of the benzyl alcohol derivative from Example 27, dissolved in 10 ml of dry dimethylformamide, were added dropwise to a suspension of 0.3 g (11 millimoles) of sodium hydride in 15 ml of dry dimethylformamide. The mixture was stirred until evolution of hydrogen had ended (after about 1 hour), and 1.56 g (11 millimoles) of iodomethane were then added dropwise while cooling with ice. The mixture was then heated at 60° C. for 5 hours. On the next day, water was added dropwise, and the precipitated solid was filtered off under suction, and dissolved in methanol at elevated temperature. When the solution was cooled to room temperature, 2 phases formed. The upper (methanol) phase was heated once again and then placed in a refrigerator. The precipitated crystals were filtered off under suction and dried. 2.1 g of the title compound of melting point 66°–68° C. were obtained in this manner.

EXAMPLE 29

(E)-4-[2-(5,6,7,8-Tetrahydro-1,3-dimethoxy-5,5,8,8-tetramethylnaphth-2-yl)-1-ethenyl]-benzyl acetate 1 g (2.7 millimoles) of the benzyl alcohol derivative from Example 27 was dissolved in 5 ml of pyridine, and 1 ml of acetic anhydride was added. The mixture was stirred overnight at room temperature, after which ice/water was added and the resulting solid was filtered off under suction, washed with water, with 0.5N HCl and again with water and dried to give 1 g of the title compound of melting point 73°–74° C.

EXAMPLE 30

(E)-4-[2-(5,6,7,8-Tetrahydro-1,3-dimethoxy-5,5,8,8-tetramethylnaphth-2-yl)-1-ethenyl]-benzylamine 10 g (27 millimoles) of the nitrile from Example 5, dissolved or suspended in 170 ml of ether, were added dropwise to a suspension of 3 g (75 millimoles) of lithium aluminum hydride in 150 ml of absolute ether at room temperature in the course of about 20 minutes. The mixture was refluxed for 3.5 hours. On the next day, the cooled reaction mixture was hydrolyzed with water and sodium sulfate solution, and the aqueous phase was extracted three times with ether. The combined ether phases were washed with water, dried over Na$_2$SO$_4$ and evaporated down to give 9.8 g of the pure title compound of melting point 59°–60° C.

EXAMPLE 31

N-Acetyl-(E)-4-[2-(5,6,7,8-tetrahydro-1,3-dimethoxy-5,5,8,8-tetramethylnaphth-2-yl)-1-ethenyl]-benzylamine 1 ml of acetyl chloride in 5 ml of absolute tetrahydrofuran was added dropwise, at 20° C., to a solution of 3 g (8 millimoles) of the benzylamine derivative from Example 30, 1.6 g (16 millimoles) of triethylamine and 50 mg of DMAP (4-N,N-dimethylaminopyridine) in 25 ml of absolute tetrahydrofuran. After 1 hour at 0° C., the mixture was poured onto 100 ml of water and extracted with methylene chloride. The organic phase was dried and evaporated down, and the oily residue was heated with heptane. The mixture was cooled, the supernatant heptane phase was decanted, and the process was repeated several times. Finally, 0.8 g of the title compound of melting point 126°–127° C. crystallized out from the heptane solution and was filtered off under suction.

EXAMPLE 32

Ethyl (E,E)-4-[2-(5,6,7,8-tetrahydro-1,3-dimethoxy-5,5,8,8-tetramethylnaphth-2-yl)-1-ethenyl]-cinnamate A solution of 3.3 g (14.8 millimoles) of ethyl diethylphosphonoacetate in 15 ml of absolute tetrahydrofuran was added dropwise to a suspension of 0.5 g (16.6 millimoles) of sodium hydride in 25 ml of absolute tetrahydrofuran. The mixture was stirred for a further hour, after which a solution of 2.8 g (7.4 millimoles) of the aldehyde described in Example 26, in 15 ml of absolute tetrahydrofuran, was added dropwise. Stirring was continued for a further 16 hours, and the mixture was poured onto water and acidified. The aqueous phase was separated off and extracted twice with ether, and the combined ether extracts were washed once with water, dried over Na$_2$SO$_4$ and evaporated down. The residue (4.8 g) was recrystallized from heptane, and 0.5 g of the title compound of melting point 205°–207° C. was obtained.

We claim:

1. A 1-substituted tetraline of the formula I

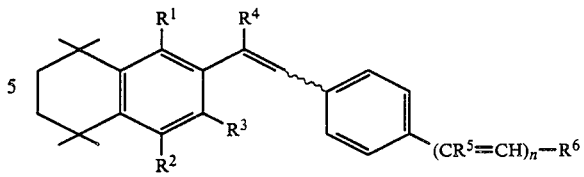

where n is 0 or 1, $R^1$ is hydroxyl or $C_1$–$C_6$-alkoxy, $R^2$ and $R^3$ are each hydrogen, halogen, $C_1$–$C_4$-alkyl or methoxy, $R^4$ is hydrogen or an acyclic or cyclic alkyl group of not more than 6 carbon atoms, $R^5$ is hydrogen or $C_1$–$C_4$-alkyl, and $R^6$ is —COOR$^{13}$, where $R^{13}$ is hydrogen or $C_1$–$C_8$-alkyl which is unsubstituted or substituted by hydroxyl or $C_1$–$C_6$-alkoxy and their physiologically tolerated salts.

2. The compound of claim 1 which is (E)-4-[2-(5,6,7,8-tetrahydro-3,5,5,8,8-pentamethyl-1-propoxy-naphth-2-yl)-1-ethenyl]-benzoic acid.

3. The compound of claim 1 which is (E)-4-[2-(1-butyloxy-5,6,7,8-tetrahydro-3,5,5,8,8-pentamethyl-naphth-2-yl)-1-ethenyl]-benzoic acid.

4. The compound of claim 1 which is (E)-4-[2-(1-ethoxy-5,6,7,8-tetrahydro-3,5,5,8,8-pentamethylnaphth-2-yl)-1-ethenyl]-benzoic acid.

5. The compound of claim 1 which is (E)-4-[2-(5,6,7,8-tetrahydro-1,3-dimethoxy-5,5,8,8-tetramethyl-naphth-2-yl)-1-ethenyl]-benzoic acid.

6. A therapeutic composition for treating dermatological disorders comprising a pharmaceutically acceptable carrier and an effective amount of a compound according to claim 1 as the active compound.

7. The method of treating dermatological disorders in a patient suffering therefrom which comprises administering an effective amount of a compound according to claim 1.

8. The method of treating dermatological disorders as set forth in claim 7, wherein an effective amount of a compound according to claim 2 is administered to the patient.

9. The method of treating dermatological disorders as set forth in claim 7, wherein an effective amount of a compound according to claim 3 is administered to the patient.

10. The method of treating dermatological disorders as set forth in claim 7, wherein an effective amount of a compound according to claim 4 is administered to the patient.

11. The method of treating dermatological disorders as set forth in claim 7, wherein an effective amount of a compound according to claim 5 is administered to the patient.

* * * * *